United States Patent
Baumgartner

(10) Patent No.: US 8,776,335 B2
(45) Date of Patent: Jul. 15, 2014

(54) METHODS OF FABRICATING ULTRASONIC TRANSDUCER ASSEMBLIES

(75) Inventor: Charles Edward Baumgartner, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 807 days.

(21) Appl. No.: 12/947,856

(22) Filed: Nov. 17, 2010

(65) Prior Publication Data

US 2012/0118475 A1    May 17, 2012

(51) Int. Cl.
| | |
|---|---|
| H03H 3/02 | (2006.01) |
| H01L 41/22 | (2013.01) |
| H01L 41/25 | (2013.01) |
| H03H 3/08 | (2006.01) |
| H03H 3/10 | (2006.01) |
| B06B 1/06 | (2006.01) |
| G01N 29/00 | (2006.01) |
| B32B 38/00 | (2006.01) |

(52) U.S. Cl.
CPC ................ *H01L 41/22* (2013.01); *H01L 41/25* (2013.01); *H03H 3/08* (2013.01); *H03H 3/10* (2013.01); *B06B 1/0622* (2013.01); *B06B 1/0629* (2013.01); *G01N 29/00* (2013.01); *B32B 38/0004* (2013.01)
USPC ................ 29/25.35; 29/594; 29/832; 29/854; 29/417; 310/313 R; 310/334; 310/340; 310/344

(58) Field of Classification Search
CPC ............. H03H 3/04; H03H 3/08; H03H 3/10; B32B 38/0004; B06B 1/0622; B06B 1/0629; H01L 41/22; H01L 41/25; G01N 29/00
USPC ........ 29/594, 25.35, 832, 854, 841, 412, 417; 310/313 R, 334, 340, 344, 348
See application file for complete search history.

(56) References Cited

U.S. PATENT DOCUMENTS 5,996,199 A * 12/1999 Ichikawa et al. ......... H03H 3/10
6,963,155 B1 * 11/2005 Wadaka et al. .......... H03H 3/04
(Continued)

FOREIGN PATENT DOCUMENTS

| JP | 63121306 A * | 5/1988 | .................... 29/25.35 |
|---|---|---|---|
| WO | 9921226 A1 | 4/1999 | |
| WO | 2006050127 A2 | 5/2006 | |

OTHER PUBLICATIONS

X. Zhuang et al., "Through-Wafer Trench-Isolated Electrical Interconnects for CMUT Arrays," IEEE Ultrasonics Symposium, 2005, pp. 475-478.

(Continued)

*Primary Examiner* — A. Dexter Tugbang
(74) *Attorney, Agent, or Firm* — Ellen B. Gallagher

(57) ABSTRACT

A method of fabricating a plurality of ultrasound transducer assemblies is provided. The method includes applying one or more layers of patternable material to at least a portion of a surface of a wafer comprising a number of die. The method further includes patterning the patternable material to define a plurality of openings, where each of the openings is aligned with a respective one of the die, disposing ultrasound acoustic arrays in respective ones of the openings, coupling the ultrasound acoustic arrays to the respective die to form the respective ultrasound transducer assemblies, and separating the ultrasound transducer assemblies to form individual ultrasound transducer assemblies.

26 Claims, 6 Drawing Sheets

(56) References Cited

U.S. PATENT DOCUMENTS

| | | |
|---|---|---|
| 7,053,530 B2 | 5/2006 | Baumgartner et al. |
| 7,156,938 B2 | 1/2007 | Baumgartner et al. |
| 7,451,651 B2 | 11/2008 | Woychik et al. |
| 2004/0191955 A1 | 9/2004 | Joshi et al. |
| 2007/0267945 A1 | 11/2007 | Sudol |
| 2009/0032940 A1 | 2/2009 | Topacio et al. |
| 2009/0105596 A1 | 4/2009 | Savord et al. |
| 2009/0156939 A1 | 6/2009 | Sadaka et al. |
| 2009/0309217 A1 | 12/2009 | Sudol |

OTHER PUBLICATIONS

B. Savord et al., "Fully Sampled Matrix Transducer for Real Time 3D Ultrasonic Imaging," IEEE Ultrasonics Symposium, 2003, vol. 1, pp. 945-953.

C. Daft et al., "Microfabricated Ultrasonic Transducers Monolithically Integrated with High Voltage Electronics," IEEE Ultrasonics, Ferroelectrics, and Frequency Control Joint 50th Anniversary Conference, 2004, vol. 1, pp. 493-496.

* cited by examiner

METHODS OF FABRICATING ULTRASONIC TRANSDUCER ASSEMBLIES

BACKGROUND

The invention relates generally to methods of fabricating sensor array assemblies and, more particularly, to sensor array assemblies, where the sensor array is coupled to electronics.

Commonly used sensor arrays include light sensors, heat sensors, and acoustic sensors. An example of an acoustic sensor is an ultrasound transducer. Ultrasonic transducer assemblies are typically employed in applications including non-destructive evaluation (NDE) and medical diagnostic imaging, such as ultrasound applications. The ultrasonic transducer assembly generally includes an array of ultrasonic transducers coupled to an electronics array. The array may be one dimensional (1D) (a linear array or row of acoustic elements) for two-dimensional (2D) imaging. Similarly, the array may be a 2D array for volumetric imaging. The ultrasonic transducer array generally includes hundreds or thousands of individual transducers. Similarly, the electronics array includes hundreds or thousands of integrated interface circuits (or "cells") which are electrically coupled to provide electrical control of the transducers for beam forming, signal amplification, control functions, signal processing, etc.

Piezoelectric transducers (PZT) are a widely used type of ultrasonic transducer. PZT sensors generally include a piezoelectric ceramic capable of changing physical dimensions when subjected to electrical or mechanical stress. Fabricating the transducer array and the electronics array, and coupling the two arrays together, provides a number of design challenges. Semiconductor based application specific integrated circuits (ASICs) are generally fabricated in wafer form and diced, providing a number of chips. PZT sensors are generally fabricated by dicing ceramic block material. Often PZT sensors are formed out of layers of ceramic, matching materials and damping materials. Each sensor sub-array typically includes many sensors. Each sensor sub-array or chip in the sensor array is typically coupled to an integrated circuit chip to provide individual control of each sensor. With hundreds or thousands of sensors and chips, each having countless electrical connections, the fabrication and assembly of such sensor assemblies can be challenging. This challenge becomes amplified when the application calls for size reduction in the sensor assembly.

Imaging transducers comprised of an acoustic array on an application specific integrated circuit are presently fabricated individually requiring a number of processing steps to be replicated for each manufactured transducer. This replication leads to a long manufacturing cycle and hence to a relatively high product cost. It would therefore be desirable to provide a process capable of manufacturing multiple electro-acoustic transducers at a time.

BRIEF DESCRIPTION OF THE INVENTION

One aspect of the present invention resides in a method of fabricating a number of ultrasound transducer assemblies. The method includes applying one or more layers of patternable material to at least a portion of a surface of a wafer comprising a number of die. The method further includes patterning the patternable material to define a number of openings, where each of the openings is aligned with a respective one of the die, disposing a number of ultrasound acoustic arrays in respective ones of the openings, coupling the ultrasound acoustic arrays to the respective die to form the respective ultrasound transducer assemblies, and separating the ultrasound transducer assemblies to form individual ultrasound transducer assemblies.

Another aspect of the present invention resides in a method of fabricating a number of acoustic transducers with one-dimensional (1D) or two-dimensional (2D) matrix arrays. The method includes applying one or more layers of resist material to at least a portion of a surface of an application specific integrated circuit (ASIC) wafer comprising a number of ASIC die. The method further includes patterning the resist material to define a number of openings, where each of the openings is aligned with a respective one of the ASIC die, disposing acoustic 1D or 2D matrix arrays in respective ones of the openings, coupling the acoustic 1D or 2D matrix arrays to the respective ASIC die to form the respective acoustic transducers, and singulating the acoustic transducers to form individual acoustic transducers with 1D or 2D matrix arrays.

DRAWINGS

These and other features, aspects, and advantages of the present invention will become better understood when the following detailed description is read with reference to the accompanying drawings in which like characters represent like parts throughout the drawings, wherein:

FIG. 1 schematically depicts an application specific integrated circuit (ASIC) wafer with a number of ASIC die;

FIGS. 2-6 are cross-sectional views of an ASIC wafer illustrating processing steps for a method of fabricating ultrasonic transducer assembles, in accordance with embodiments of the present invention;

FIG. 7 schematically depicts four individual ultrasonic transducer assembles fabricated using the method illustrated in FIGS. 2-6;

DETAILED DESCRIPTION OF THE INVENTION

The terms "first," "second," and the like, herein do not denote any order, quantity, or importance, but rather are used to distinguish one element from another. The terms "a" and "an" herein do not denote a limitation of quantity, but rather denote the presence of at least one of the referenced items. The modifier "about" used in connection with a quantity is inclusive of the stated value, and has the meaning dictated by context, (e.g., includes the degree of error associated with measurement of the particular quantity). In addition, the term "combination" is inclusive of blends, mixtures, alloys, reaction products, and the like.

Moreover, in this specification, the suffix "(s)" is usually intended to include both the singular and the plural of the term that it modifies, thereby including one or more of that term (e.g., "the passage hole" may include one or more passage holes, unless otherwise specified). Reference throughout the specification to "one embodiment," "another embodiment," "an embodiment," and so forth, means that a particular element (e.g., feature, structure, and/or characteristic) described in connection with the embodiment is included in at least one embodiment described herein, and may or may not be present in other embodiments. In addition, it is to be understood that the described inventive features may be combined in any suitable manner in the various embodiments.

Figure 1:
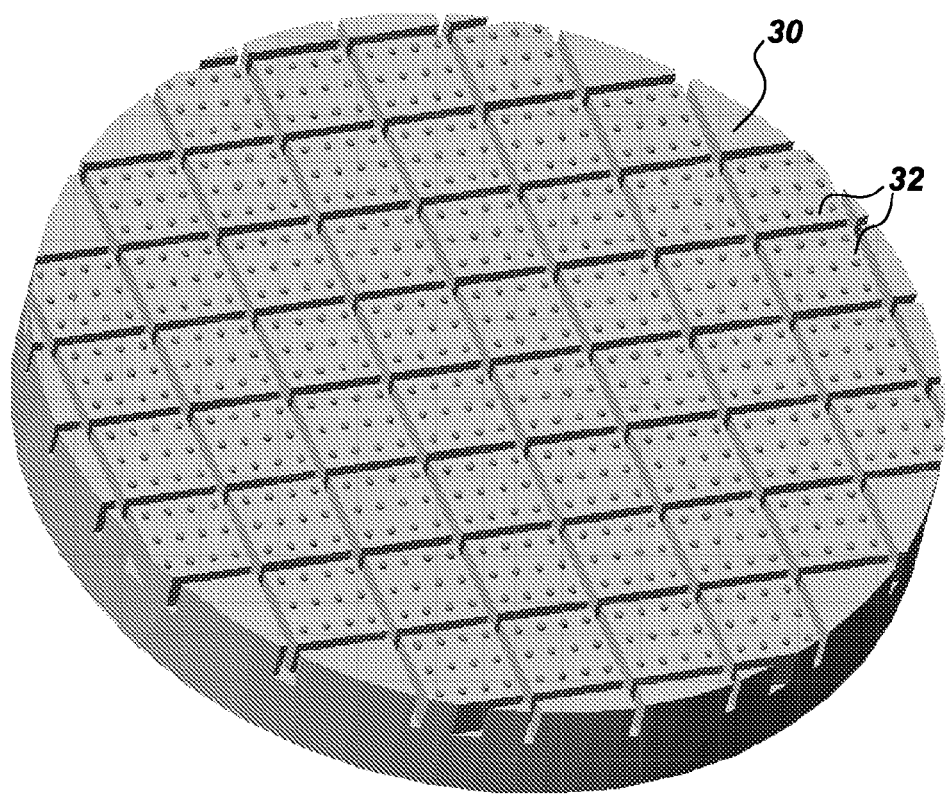
Figure 2:
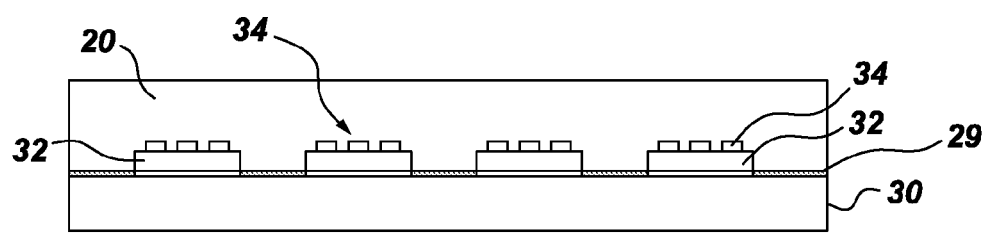
Figure 8:
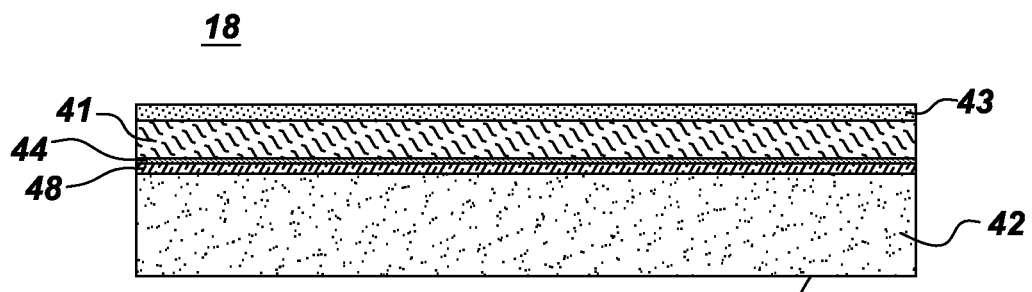
FIG. 8 illustrates an example acoustic stack.
Figure 9:
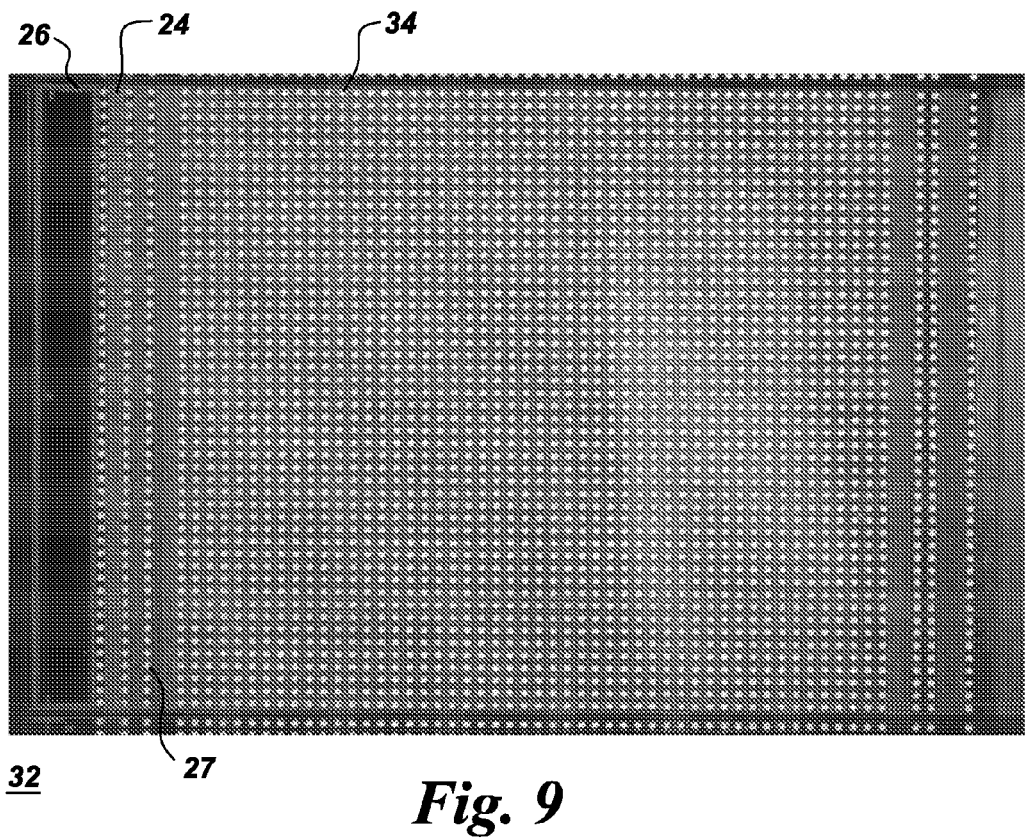
FIG. 9 is a top view of a of bump-plated ASIC die for use in forming the ultrasonic transducer assemblies fabricated using the method illustrated in FIGS. 2-6.

A method of fabricating a number of ultrasonic transducer assemblies 10 is described with reference to FIGS. 1-15. As indicated for example in FIGS. 2 and 10, the method includes at step 60 applying one or more layers of patternable material 20 to at least a portion of a surface of a wafer 30 having a number of die 32. For particular embodiments, the wafer 30 comprises an application specific integrated circuit (ASIC) wafer, one example of which is depicted in FIG. 1. As indicated in FIG. 1, the ASIC wafer 30 includes a number of ASIC die 32, and FIG. 9 shows an example ASIC die 32. The ASIC die 32 include circuitry for performing desired functions and may include a variety of electrical components, including without limitation, transistors, resistors and capacitors. For the case of ultrasonic transducer assemblies, the ASICs may be used to reconfigure the array structure or to process the acoustic signals from different array elements, for example. For ease of illustration, only four ASIC die 32 are shown in FIGS. 2-7. However, the wafer 30 will typically include larger arrays of ASIC die, for example a standard 8 inch wafer may contain 200 or more one centimeter square die or more than a thousand 250 millimeter square die. In addition, it should be noted that although the die shown in the figures include bumps 34 for connection to the acoustic array, for other example configurations, the array may contain the bumps, while the ASIC possesses bonding pads only. For both configurations, the bumps may be electroplated, stud bumps, solder bumps, etc. and are used for interconnect to the transducer elements, as discussed below with reference to FIGS. 9 and 12.

Figure 3:
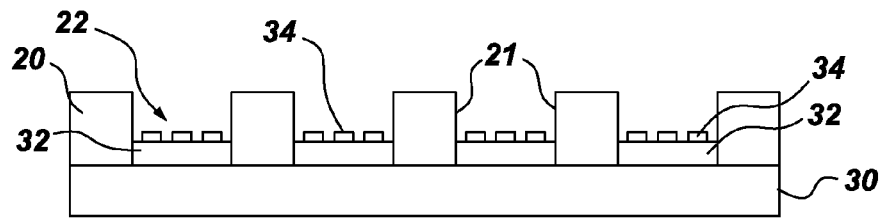
Figure 10:
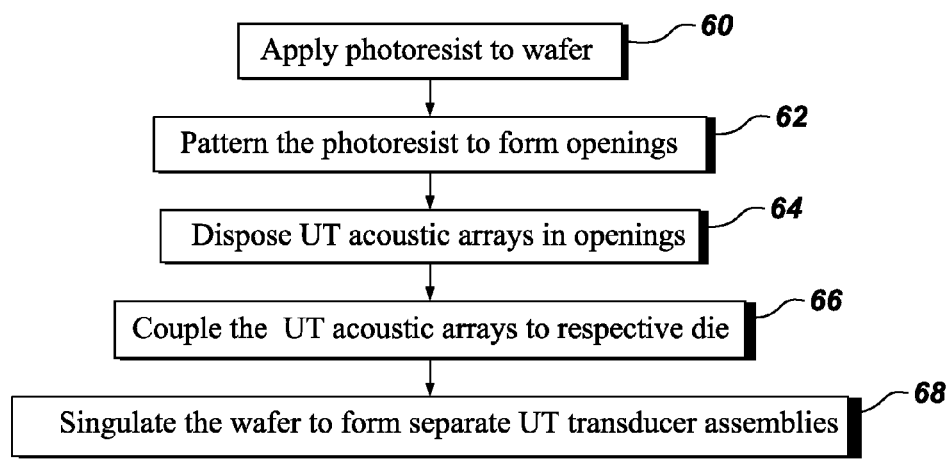
FIG. 10 is a flow diagram illustrating a method of fabricating ultrasonic transducer assemblies.

As indicated, for example, in FIGS. 3 and 10, the method further includes at step 62, patterning the patternable material 20 to define a number of openings 22. As indicated in FIG. 3, each of the openings 22 is aligned with a respective one of the die 32. For particular arrangements, the patternable material 20 comprises photoresist, and the patterning step 62 comprises performing photolithography to form the openings 22. Non-limiting examples of suitable photoresists include materials selected from the SU-8 photoresist product line, which is commercially available from MicroChem, which has a place of business in Newton, Mass. For particular examples the photoresist 20 is a negative photoresist, and the openings 22 are formed by disposing a lithographic mask (not shown) on the wafer 30 and applying light to remove the exposed photoresist 20. For other arrangements, other types of resist may be employed. For particular configurations, the patternable material 20 is patterned such that the openings 22 have side walls 21 with an aspect ratio of at least ten. According to more particular examples, the side walls 21 of the openings 22 have an aspect ratio of at least fifteen, and more particularly, of at least twenty. In one non-limiting example, a layer 20 of SU-8 photoresist with a thickness of up to about 5 mm is applied. The openings 22 will correspond to the area on each die 32 that will ultimately be bonded to an acoustic array. The resist remaining around the openings forms a pocket into which an acoustic array will fit.

Figure 4:
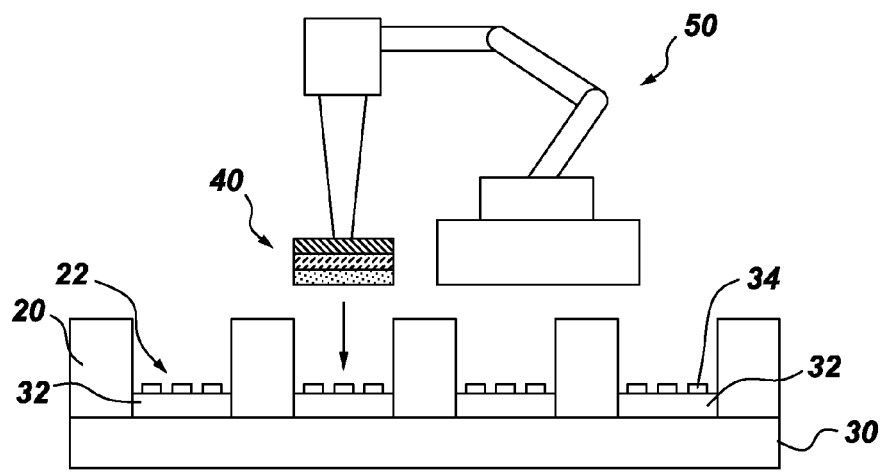
Figure 5:
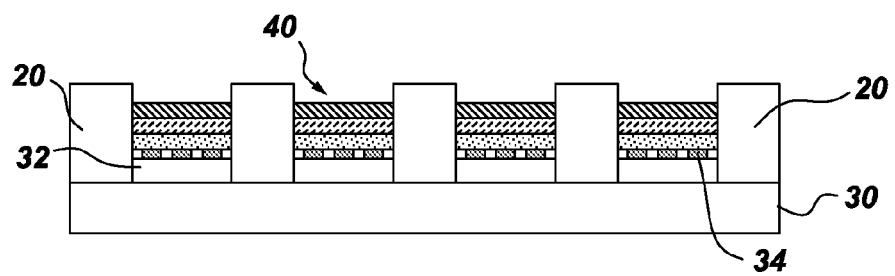

Referring to FIGS. 4, 5 and 10, the method further includes at step 64 disposing a number of ultrasonic acoustic arrays 40 in respective ones of the openings 22. Beneficially, the patterned material 20 opening 22 acts as a key-hole to both accurately align and hold the acoustic arrays in place on the wafer 30. For the particular arrangement shown in FIG. 4, the ultrasonic acoustic arrays 40 are disposed within the openings 22 using a pick-and-place machine 50. Numerically controlled pick-and-place machines (also termed "surface mount technology component placement systems") are known in the art and are typically used to place surface mount devices (electrical components) on printed circuit boards. Pick-and-place machines typically include pneumatic suction nozzles, and each nozzle head can be manipulated in three dimensions and rotated independently.

Figure 6:
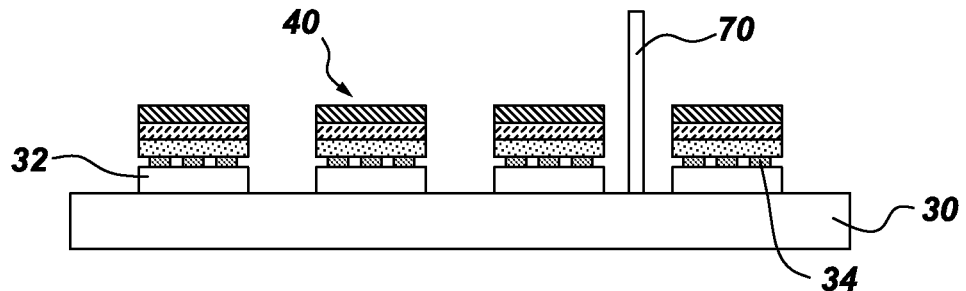
Figure 7:
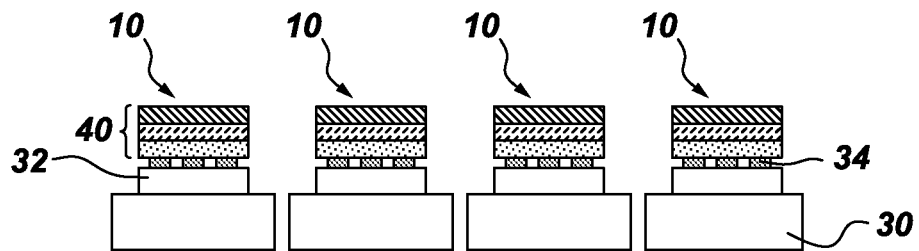

As indicated, for example, in FIGS. 5 and 10, the method further includes at step 66, coupling the ultrasonic acoustic arrays 40 to the respective die 32 to form the respective ultrasonic transducer assemblies 10. Techniques for coupling the ultrasonic acoustic arrays 40 to the die 32 are discussed below. Referring to FIGS. 6, 7 and 10, the method further includes at step 68, separating the ultrasonic transducer assemblies to form individual ultrasonic transducer assemblies 10. For the example arrangement shown in FIG. 6, a dicing saw 70 may be used to singulate each of the sensor assemblies 10, as indicated, for example in FIG. 7.

Figure 11:
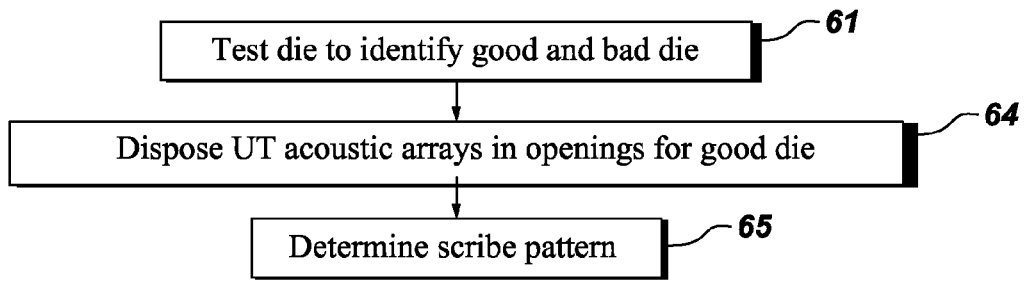
FIGS. 11 and 12 are flow diagrams illustrating additional optional steps for the method shown in FIG. 10.

FIG. 11 illustrates additional, optional steps for the method of fabricating ultrasonic transducer assemblies. For the example process shown in FIG. 11, prior to disposition of the ultrasonic acoustic arrays 40, the die 32 may be tested at step 61 to identify good die and bad die. For this example, the ultrasonic acoustic arrays 40 are disposed only at the good die in step 64. As indicated in FIG. 11, the method further optionally includes at step 65 determining a scribe pattern for separating the ultrasonic transducer assemblies 10. The scribe pattern may be determined after the good and bad die are identified. However, typically, all of the die will be separated. However, for this particular process configuration, only the good die will have been bonded to ultrasonic acoustic arrays 40. Beneficially, determining the scribe pattern after electrical testing results in identification of the maximum number of functional ultrasonic transducer assemblies 10.

Typically the acoustic arrays 40 are formed by assembling a piezoelectric ceramic layer, with one or more acoustic matching layers. For the example arrangement shown in FIG. 8, the acoustic stack 18 comprises a piezoelectric ceramic layer 42 (for example, PZT). The front and rear faces 44, 46 are metal coated for the illustrated example. As shown in FIG. 8, a conductive foil 48 is bonded to the metal coated front face 44 of the PZT layer 42, and a first acoustic impedance matching layer 41 is bonded to the conductive foil 48. Non-limiting examples of matching layer 41 include metal filled graphite, ceramic powder filled epoxy, glass, and glass-ceramics. Non-limiting examples of outer matching layer 43 include ABS plastic, polyethylene, polystyrene, and unfilled epoxy. Other materials with similar acoustic impedances may be used as well. The matching layer 41 has an acoustic impedance less than that of the piezoelectric ceramic layer 42. For the illustrated example, a second acoustic impedance matching layer 43 having an acoustic impedance less than that of the first acoustic impedance matching layer 41 is bonded to the front face of the first matching layer 41. Beneficially, the acoustic impedance matching layers 41, 43 transform the relatively high acoustic impedance of the piezoelectric ceramic to the low acoustic impedance of the human body and water, thereby improving the coupling with the medium in which the emitted ultrasonic waves will propagate. Although the illustrated example includes two acoustic impedance matching layer, other arrangements may include only one acoustic impedance matching layer, or more than two acoustic impedance matching layers located in front of or behind the PZT. In addition, a matching layer possessing an acoustic impedance greater than the PZT may be placed behind the PZT in the acoustic array. Non-limiting examples of this de-matching layer includes heavy metals, such as molybdenum or tungsten, and high density ceramics, such as tungsten carbide.

Figure 13:
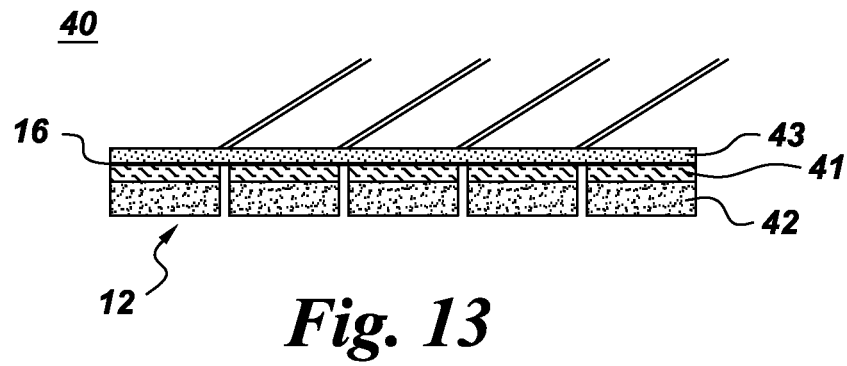
FIG. 13 illustrates five linear rows of acoustic elements separated by dicing kerfs.

Typically, the assembled piezoelectric ceramic and acoustic impedance matching layers 42, 41, 43 (that is, the acoustic stack 18) are diced into individual elements prior to being disposed in openings 22 and coupled to the respective die 32. For example and as indicated in FIG. 13, the assembled piezoelectric ceramic and acoustic impedance matching layer(s) 42, 41, 43 may be diced into linear rows (linear arrays) 12 of acoustic elements prior to being disposed in the openings 22, such that a number of dicing kerfs 14 are formed between neighboring ones of the linear rows 12 of acoustic elements. (For ease of illustration the conductive foil 48 discussed above with reference to FIG. 8 is not shown in FIG. 13.) As known in the art, linear arrays 12 of transducer elements are used for two-dimensional (2D) imaging. In order to hold the linear rows 12 of acoustic elements together prior to being disposed in the openings 22, for this process configuration, the method may further optionally include disposing an electrically non-conductive material into the dicing kerfs 14, or, as shown in FIG. 13, the top matching layer 43 can be undiced to provide support for the linear rows 12. Non-limiting examples of suitable electrically non-conductive materials include silicone. For the specific configuration shown in FIG. 13, the assembled piezoelectric ceramic and acoustic impedance matching layer(s) 42, 41, were diced, and then the second acoustic impedance matching layer 43 was disposed over the linear arrays 12. More generally, the method may optionally further include disposing an electrically non-conductive material (for example, the second acoustic impedance matching layer 43) on an upper surface 16 of the linear rows 12 of acoustic elements to hold the linear rows 12 together prior to being disposed in the openings 22.

Figure 14:
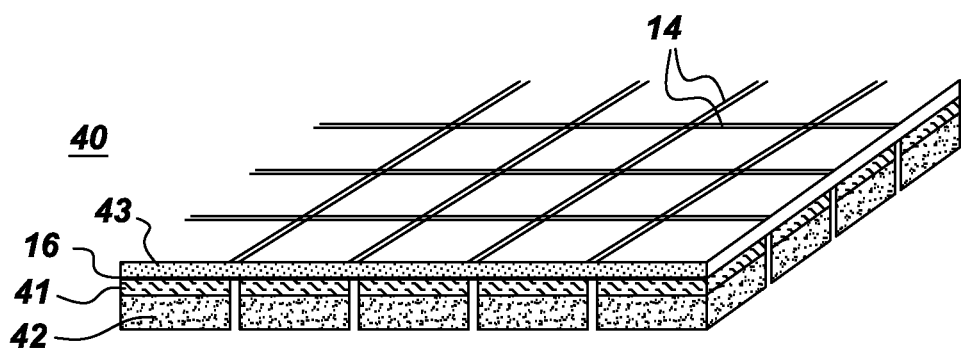
FIG. 14 illustrates an example two-dimensional array of acoustic elements.

Similarly, instead of dicing the acoustic stack 18 (see FIG. 8) into linear rows 12 prior to coupling with the respective die 32, the acoustic stack 18 may be diced into a two dimensional (2D) array of acoustic elements 40 prior to being disposed in a respective opening 22, as indicated, for example in FIG. 14. More particularly, the method may further comprise dicing the assembled piezoelectric ceramic and at least one acoustic impedance matching layer 42, 41, 43 into respective two-dimensional (2D) arrays 40 of acoustic elements prior to being disposed in the openings 22, such that a number of dicing kerfs 14 are formed between neighboring ones of the acoustic elements, as indicated in FIG. 14, for example. As known in the art, 2D arrays of transducer elements are used for volumetric imaging. In order to hold the 2D array of acoustic elements together prior to being disposed in the openings 22, for this process configuration, the method may further optionally include disposing an electrically non-conductive material (for example, silicone) into the dicing kerfs 14. For the specific configuration shown in FIG. 14, the assembled piezoelectric ceramic and acoustic impedance matching layer(s) 42, 41, were diced, and then the second acoustic impedance matching layer 43 was disposed over the 2D array 40. More generally, the method may optionally further include disposing an electrically non-conductive material (for example, the second acoustic impedance matching layer 43) on an upper surface 16 of the respective 2D array 40 of acoustic elements to hold the respective 2D arrays 40 together prior to being disposed in the openings 22.

Typically, after fabrication, the array 12, 40 is cut to the required final dimensions. For example, if the final product requires an acoustic array that is 10 mm×25 mm, the initial structure may be fabricated, for example, using components that are 50 mm×25 mm. Then, once fabrication of the larger piece is completed, five separate parts may be formed at 10 mm×25 mm each, for this example. Typically, the acoustic stack 18 will be diced into a set of multiple linear or 2D arrays and then cut to the required final dimensions. Alternately, the process may be reversed, that is the acoustic stack 18 may be cut to final dimensions first and then diced into 1D or 2D arrays of transducer elements.

For other process configurations, the assembled piezoelectric ceramic and acoustic impedance matching layers (42,41, 43) are cut to the required final dimensions prior to disposition in the openings 20 but are diced (for example, into linear rows 12 or into 2D arrays 40) of acoustic elements) after disposing the cut-to-size, assembled layers (acoustic stack 18) in the respective opening 22.

Figure 12:
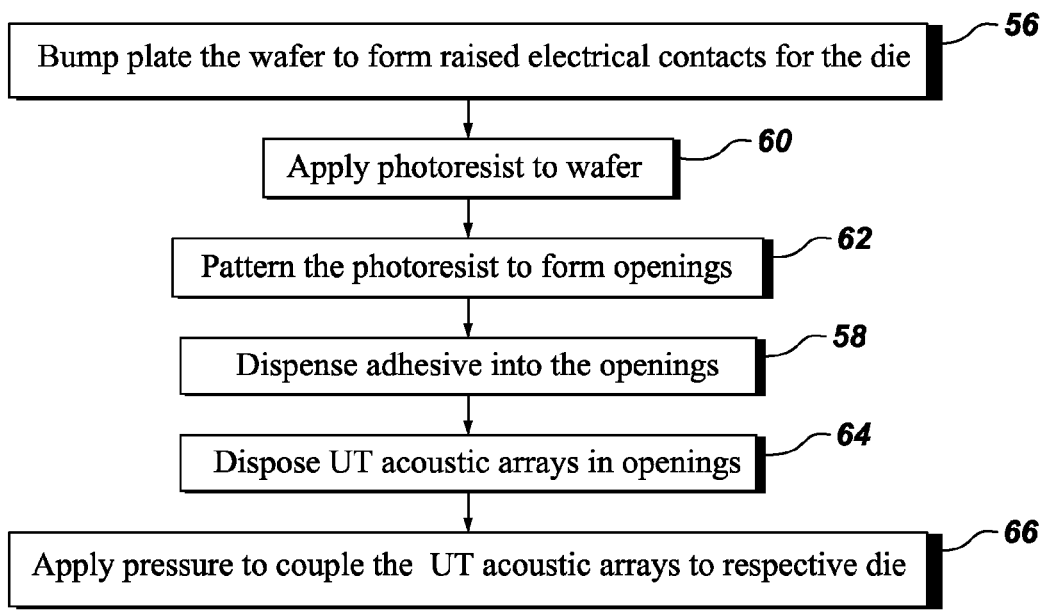

FIG. 12 illustrates additional, optional steps for the method of fabricating ultrasonic transducer assemblies. For the example process shown in FIG. 12, the method further optionally includes, at step 58, dispensing an adhesive into the openings 22 prior to disposing the ultrasonic acoustic arrays 40 in the openings 22 and applying pressure, such that electrical connections are developed between the two surfaces until the adhesive is cured. For example, a controlled quantity of adhesive, such as a non-electrically conductive epoxy, may be dispensed into the openings 22. Non-limiting examples of suitable adhesives include a two-component, high temperature epoxy, marketed under the tradename Epo-tek® 353nd, a two component epoxy resin marketed under the tradename Epo-tek® 301-2FL, an underfill adhesive marketed under the tradename Namics U8443, a capillary underflow adhesive marketed under the tradename Emerson & Cuming e1172a™, or other non-conducting underfill adhesives. For alternate arrangements, the adhesive may comprise an anisotropically conductive adhesive with pressure and temperature applied to cause electrical connections between the mating surfaces. For the particular process of FIG. 11, if the optional testing step 61 is included, then the adhesive is deposited only into those die identified as being good die.

For the particular process shown in FIG. 12, the method further optionally includes, at step 56, bump plating the respective areas on the wafer 20 corresponding to the die 32 to form raised electrical contacts 34 for the respective die. For example solder bumps 34 may be formed on the surface of the die 32. For the example ASIC die 32 shown in FIG. 9, the raised electrical contacts 34 are gold plated. In one non-limiting example, bump height is not critical, and a plated height of 5 micrometers can be used. More particularly, and as indicated in FIG. 12, following the bump plating step 56, a photo-definable material, such as a thick film resist, is applied to the wafer 30, at step 60, and patterned, at step 62, to expose the bumped or contact areas while leaving a thick resist layer (FIG. 3) present on the remaining wafer 30. According to a more particular embodiment, each of the ultrasonic acoustic arrays 40 comprises an electrically conducting rear face 46 (see FIG. 8), and the ultrasonic acoustic arrays 40 are disposed in the openings 22, such that the rear face 46 of each of the ultrasonic acoustic arrays 40 faces the respective die 32. The method further optionally includes, at step 58, dispensing an adhesive (for example, an epoxy) into the openings 22 prior to disposing the ultrasonic acoustic arrays 40 in the openings 22 and, at step 66, applying pressure to the ultrasonic acoustic arrays 40 after their disposition in the openings 22 to bring the rear face 46 of each of the ultrasonic acoustic arrays 40 in electrical contact with the raised electrical contacts 34 of the respective die 32. More particularly, the pressure is applied until the adhesive has been cured. Beneficially, the patterned resist 20 opening 22 acts as a key-hole to both accurately align and hold the acoustic arrays in place on the wafer 30, such that the ASIC bumps 34 align with the acoustic array elements. After the adhesive has been cured, the remaining photo-definable material may or may not be stripped from the wafer 30 prior to dicing to separate the acoustic transducers (array on ASIC) from one another. For example, the remaining resist material may be removed from the wafer surface, if desired, using either a global method, such as dissolution in a solvent, or in specific locations, for example by use of a laser.

For particular processes, the method further includes removing the remaining patternable material 20 from the wafer 30 after the ultrasonic acoustic arrays 40 have been coupled to the respective die 32. For example, the remaining photoresist material may be removed from the wafer 30 surface using a global technique, such as dissolution in a solvent, or from specific locations, for example using a laser. Further, the remaining resist may be removed before or after singulation of the ultrasonic transducer assemblies 10.

Figure 15:
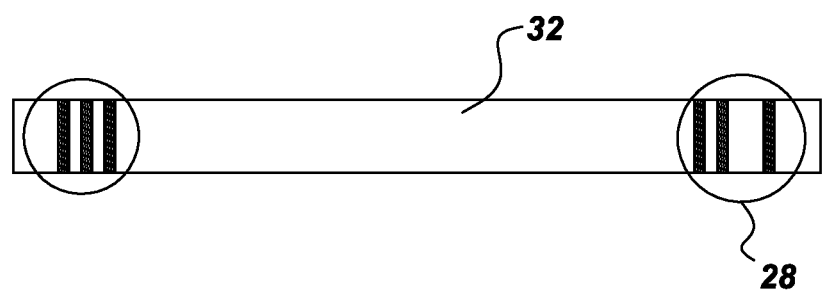
FIG. 15 is a cross-sectional view of the bump-plated ASIC die shown in FIG. 9 and schematically depicts through silicon vias (TSVs) for the ASIC die.

The method further optionally includes the step of forming a number of power, control and signal connections 24, 26 to the respective ultrasonic transducer assemblies 10. For the example configuration shown in FIG. 9, the power and control connections 24, signal connections 26 and ground 27 are formed in a rear face 29 (see FIG. 2) of the wafer 30 by forming through vias 28 in the wafer 30, as indicated in FIG. 15. For this configuration, the connections 24, 26, 27 may advantageously be formed using through silicon vias (TSVs) in the wafer using known TSV techniques prior to singulation of the ultrasonic transducer assemblies 10. Typically, TSV vias are fabricated in a silicon chip, and the vias are filled with metal, such as copper, gold, tungsten, or solder, or with a highly-doped semiconductor material, such as polysilicon. For configurations where the interconnect to the die is made on the backside using TSVs, the patternable material may be left on the wafer surface.

For other processes, the method further includes wire-bonding a number of power, control and signal connections to the respective ultrasonic transducer assemblies 10. For this configuration, the connections are formed to ASIC pads (not shown) separate from the acoustic components, after singulation of the ultrasonic transducer assemblies 10 and after removal of the remaining resist 20.

In addition to the above-described general method of fabricating ultrasonic transducer assemblies 10, a more specific method is provided for fabricating acoustic transducers 10 with two-dimensional (2D) matrix arrays. As indicated for example in FIGS. 2 and 10, the method includes at step 60, applying one or more layers of resist material 20 to at least a portion of a surface of an application specific integrated circuit (ASIC) wafer 30 containing a number of ASIC die 32. As indicated in FIGS. 3 and 10, the method further includes at step 62, patterning the resist material 20 to define a number of openings. As indicated in FIG. 3, each of the openings is aligned with a respective one of the ASIC die 32. This alignment may be achieved, for example, using a photolithographic mask (not shown) for the ASIC wafer 30.

As indicated in FIGS. 4, 5 and 10, the method for fabricating acoustic transducers 10 with two-dimensional (2D) matrix arrays further includes, at step 64, disposing a number of acoustic 2D matrix arrays 40 in respective ones of the openings 22. For the particular arrangement shown in FIG. 4, the acoustic 2D matrix arrays 40 are disposed within the openings 22 using a numerically-controlled pick-and-place machine 50. For the example process shown in FIG. 11, prior to disposition of the acoustic 2D matrix arrays 40, the die 32 may optionally be tested at step 61 to identify good die and bad die. For this example, the acoustic 2D matrix arrays 40 are disposed only at the good die in step 64.

As indicated, for example, in FIGS. 5 and 10, the method for fabricating acoustic transducers 10 with two-dimensional (2D) matrix arrays further includes, at step 66, coupling the acoustic 2D matrix arrays 40 to the respective ASIC die 32 to form the respective acoustic transducers 10. Techniques for coupling the acoustic 2D matrix arrays 40 to the ASIC die 32 are discussed below. As indicated in FIGS. 6, 7 and 10, the method for fabricating acoustic transducers 10 with two-dimensional (2D) matrix arrays further includes, at step 68, singulating the acoustic transducers to form individual acoustic transducers with 2D matrix arrays 10. For the example arrangement shown in FIG. 6, a dicing saw 70 may be used to singulate each of the acoustic transducers 10, as indicated, for example in FIG. 7.

For particular process configurations, the resist material 20 comprises photoresist 20, and the patterning step 62 comprises performing photolithography to form the openings 22. For these specific process configurations, the method further includes, at step 56, bump plating the respective areas on the ASIC wafer 20 corresponding to the ASIC die 32 to form respective sets of raised electrical contacts 34, as indicated for example in FIG. 2. For example solder bumps 34 may be formed on the surface of the die 32.

More particularly, each of the acoustic 2D matrix arrays 40 comprises an electrically conducting rear face 46 (see FIG. 8), and the acoustic 2D matrix arrays 40 are disposed in the openings 22, such that the rear face 46 of each of the acoustic 2D matrix arrays 40 faces the respective ASIC die 32. As indicated in FIG. 12, the method further optionally includes, at step 58, dispensing an adhesive into the openings 22 prior to disposing the acoustic 2D matrix arrays 40 in the openings 22, and, at step 66, applying pressure to the acoustic 2D matrix arrays 40 after their disposition in the openings 22, in order to bring the rear face 46 of each of the acoustic 2D matrix arrays 40 in electrical contact with the raised electrical contacts 34 of the respective ASIC die 32. More particularly, pressure is applied until the adhesive has been cured. The method further optionally includes removing the remaining photoresist 20 from the ASIC wafer 30 after the acoustic 2D matrix arrays 40 have been coupled to the respective ASIC die 32.

In addition, the method may further optionally include forming power, control and signal connections 24, 26 to the respective acoustic transducers 10 in the rear face 29 of the ASIC wafer 30 by forming through silicon vias (TSVs) 28 in the ASIC wafer 30. Example power, control and signal connections 24, 26 are shown in FIG. 9, and example TSVs are schematically depicted in FIG. 15. As noted above, the TSVs 28 may be formed in the ASIC wafer 30 using known TSV techniques prior to singulation of the ultrasonic transducer assemblies 10. In addition, the remaining resist may be removed before or after singulation of the ultrasonic transducer assemblies.

Beneficially, the above-described method for fabricating acoustic transducer assemblies is performed prior to dicing the ASIC wafer, i.e., at the wafer level. Thus, the method is used to fabricate multiple acoustic transducer assemblies at a time, which may beneficially result in reduced manufacturing cost per part as well as higher volume capability for a given set of manufacturing resources.

Although only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of fabricating a plurality of ultrasound transducer assemblies, the method comprising:
    applying one or more layers of patternable material to at least a portion of a surface of a wafer comprising a plurality of dies;
    patterning the patternable material to define a plurality of openings, wherein each of the openings is aligned with a respective one of the dies;
    disposing a plurality of ultrasound acoustic arrays in respective ones of the openings;
    coupling the ultrasound acoustic arrays to the respective die to form the respective ultrasound transducer assemblies; and
    separating the ultrasound transducer assemblies to form individual ultrasound transducer assemblies.

2. The method of claim 1, wherein the patternable material comprises photoresist, and wherein the step of patterning comprises performing photolithography to form the openings.

3. The method of claim 1, wherein each of the ultrasound acoustic arrays comprises a piezoelectric ceramic layer that is assembled with at least one acoustic impedance matching layer.

4. The method of claim 3, further comprising dicing the assembled piezoelectric ceramic and the at least one acoustic impedance matching layer into linear rows of acoustic elements prior to the ultrasound acoustic arrays being disposed in the openings, such that a plurality of dicing kerfs are formed between neighboring ones of the linear rows of acoustic elements.

5. The method of claim 4, further comprising disposing an electrically non-conductive material into the dicing kerfs to hold the linear rows of acoustic elements together prior to the ultrasound acoustic arrays being disposed in the openings.

6. The method of claim 4, further comprising disposing a material on an upper surface of the linear rows of acoustic elements to hold the linear rows together prior to the ultrasound acoustic arrays being disposed in the openings.

7. The method of claim 3, further comprising dicing the assembled piezoelectric ceramic and the at least one acoustic impedance matching layers into respective two-dimensional (2D) arrays of acoustic elements prior to the ultrasound acoustic arrays being disposed in the openings, such that a plurality of dicing kerfs are formed between neighboring ones of the acoustic elements.

8. The method of claim 7, further comprising disposing an electrically non-conductive material into the dicing kerfs to hold the respective 2D arrays of acoustic elements together prior to the ultrasound acoustic arrays being disposed in the openings.

9. The method of claim 7, further comprising disposing a material on an upper surface of the respective 2D array of acoustic elements to hold the respective 2D arrays together prior to the ultrasound acoustic arrays being disposed in the openings.

10. The method of claim 3, further comprising dicing the assembled piezoelectric ceramic layer and the at least one acoustic impedance matching layer into linear rows of acoustic elements after disposing the ultrasound acoustic array in the respective opening.

11. The method of claim 3, further comprising dicing the assembled piezoelectric ceramic and the at least one acoustic impedance matching layer into two-dimensional (2D) arrays of acoustic elements after disposing the ultrasound acoustic array in the respective opening.

12. The method of claim 1, wherein the ultrasound acoustic arrays are disposed within the openings using a pick-and-place machine.

13. The method of claim 1 further comprising:
    testing the die to identify a good die and a bad die, wherein the step of disposing the ultrasound acoustic arrays comprises disposing the ultrasound acoustic arrays only at the good die; and
    determining a scribe pattern for separating the ultrasound transducer assemblies.

14. The method of claim 1, further comprising dispensing an adhesive into the openings prior to disposing the ultrasound acoustic arrays in the openings.

15. The method of claim 1, further comprising bump plating the respective areas on the wafer corresponding to the die to form respective pluralities of raised electrical contacts.

16. The method of claim 15, wherein each of the ultrasound acoustic arrays comprises an electrically conducting rear face, and wherein the ultrasound acoustic arrays are disposed in the openings such that the rear face of each of the ultrasound acoustic arrays faces the respective die, the method further comprising:
    dispensing an adhesive into the openings prior to disposing the ultrasound acoustic arrays in the openings; and
    applying pressure to the ultrasound acoustic arrays after their disposition in the openings to bring the rear face of each of the ultrasound acoustic arrays in electrical contact with the raised electrical contacts of the respective die.

17. The method of claim 1, further comprising removing the remaining patternable material from the wafer after the ultrasound acoustic arrays have been coupled to the respective die.

18. The method of claim 17, further comprising wirebonding a plurality of power, control and signal connections to the respective ultrasound transducer assemblies.

19. The method of claim 1, further comprising forming a plurality of power, control and signal connections to the respective ultrasound transducer assemblies.

20. The method of claim 19, wherein the power, control and signal connections are formed in a rear face of the wafer by forming through vias in the wafer.

21. The method of claim 1, wherein the wafer comprises an application specific integrated circuit (ASIC) wafer and wherein each of the dies comprise an ASIC.

22. The method of claim 1, wherein the patternable material is patterned such that the openings have side walls with an aspect ratio of at least ten.

23. A method of fabricating a plurality of acoustic transducers with one dimensional (1D) or two-dimensional (2D) matrix arrays, the method comprising:
    applying one or more layers of resist material to at least a portion of a surface of an application specific integrated circuit (ASIC) wafer comprising a plurality of ASIC dies;
    patterning the resist material to define a plurality of openings, wherein each of the openings is aligned with a respective one of the ASIC dies;
    disposing a plurality of acoustic 1D or 2D matrix arrays in respective ones of the openings;
    coupling the acoustic 1D or 2D matrix arrays to the respective ASIC die to form the respective acoustic transducers; and
    singulating the acoustic transducers to form individual acoustic transducers with 1D or 2D matrix arrays.

24. The method of claim 23, wherein the resist material comprises photoresist, wherein the step of patterning comprises performing photolithography to form the openings, and wherein the method further comprises bump plating the respective areas on the ASIC wafer corresponding to the ASIC die to form respective pluralities of raised electrical contacts.

25. The method of claim 23, wherein each of the acoustic 1D or 2D matrix arrays comprises an electrically conducting rear face, and wherein the acoustic 1D or 2D matrix arrays are disposed in the openings such that the rear face of each of the acoustic 1D or 2D matrix arrays faces the respective ASIC die, the method further comprising:
  dispensing an adhesive into the openings prior to disposing the acoustic 1D or 2D matrix arrays in the openings;
  applying pressure to the acoustic 1D or 2D matrix arrays after their disposition in the openings to bring the rear face of each of the acoustic 1D or 2D matrix arrays in electrical contact with the raised electrical contacts of the respective ASIC die; and
  removing the remaining photoresist from the ASIC wafer after the acoustic 1D or 2D matrix arrays have been coupled to the respective ASIC die.

26. The method of claim 23, further comprising forming a plurality of power, control and signal connections to the respective acoustic transducers in a rear face of the ASIC wafer by forming through silicon vias (TSVs) in the ASIC wafer.

* * * * *

UNITED STATES PATENT AND TRADEMARK OFFICE
CERTIFICATE OF CORRECTION

| | | |
|---|---|---|
| PATENT NO. | : 8,776,335 B2 | Page 1 of 1 |
| APPLICATION NO. | : 12/947856 | |
| DATED | : July 15, 2014 | |
| INVENTOR(S) | : Baumgartner | |

It is certified that error appears in the above-identified patent and that said Letters Patent is hereby corrected as shown below:

On the Title Page, in Item [74], under "Attorney, Agent, or Firm", in Column 2, Line 1, delete "Ellen" and insert -- Eileen --, therefor.

In the Specification

Column 6, Line 14, delete "openings 20" and insert -- openings 22 --, therefor.

Column 6, Line 43, delete "wafer 20" and insert -- wafer 30 --, therefor.

Column 8, Line 15, delete "arrays 10." and insert -- arrays 40. --, therefor.

Column 8, Line 24, delete "ASIC wafer 20" and insert -- ASIC wafer 30 --, therefor.

Signed and Sealed this
Third Day of February, 2015

Michelle K. Lee
*Deputy Director of the United States Patent and Trademark Office*